(12) United States Patent
Kairi

(10) Patent No.: US 6,851,559 B2
(45) Date of Patent: Feb. 8, 2005

(54) ANALYZING AND SORTING OF WOOD VENEERS

(75) Inventor: Matti Kairi, Lohja (FI)

(73) Assignee: Finnforest Oy, Lohja (FI)

( * ) Notice: Subject to any disclaimer, the term of this patent is extended or adjusted under 35 U.S.C. 154(b) by 110 days.

(21) Appl. No.: 10/234,404

(22) Filed: Sep. 3, 2002

(65) Prior Publication Data

US 2003/0042180 A1 Mar. 6, 2003

(30) Foreign Application Priority Data

Sep. 4, 2001 (FI) .............................................. 20011755

(51) Int. Cl.$^7$ ................................................ B07C 5/14
(52) U.S. Cl. ........................ 209/518; 209/521; 209/567; 209/571
(58) Field of Search ................................ 209/517, 518, 209/567, 571, 572, 521, 587

(56) References Cited

U.S. PATENT DOCUMENTS

| | | | |
|---|---|---|---|
| 4,739,249 A | 4/1988 | Nyfors et al. | |
| 5,335,790 A | 8/1994 | Geiger et al. | |
| 5,524,771 A | 6/1996 | Kairi et al. | |
| 6,175,092 B1 * | 1/2001 | Binette et al. | .............. 209/587 |

FOREIGN PATENT DOCUMENTS

| | | |
|---|---|---|
| DE | 4 104 501 | 9/1991 |
| DE | 93 15 506 U1 | 12/1993 |
| DE | 4 421 763 | 3/1995 |
| EP | 0 616 209 | 9/1994 |
| JP | 08-035940 | 2/1996 |
| WO | 00/25115 | 5/2000 |

OTHER PUBLICATIONS

Pertti V. Vainikainen et al., "Radiowave Sensor for Measuring the Properties of Dielectric Sheets: Application to Veneer Moisture Content and Mass per Unit Area Measurement", IEEE Transactions on Instrumentation and Measurement vol. IM–36, No. 4, Dec. 1987.

James D. Logan. P.E., "Machine Sorting of Wood for Structural LVL Applications", Washington State University, 34$^{th}$ International Particleboard/Composite Materials Symposium Proceedings, Apr. 4–6, 2000, pp. 1–13.

* cited by examiner

*Primary Examiner*—Donald P. Walsh
*Assistant Examiner*—Kaitlin Joerger
(74) *Attorney, Agent, or Firm*—Hogan & Hartson, LLP

(57) ABSTRACT

The invention relates to a method for increasing strength and/or reducing strength variations in multi-layer wood, plywood, and the like sandwich material. The method comprises measuring wood veneers (10) for dry substance density ($\rho$) with high-frequency electromagnetic resonance (TEM) and additionally analyzing the homogeneity and/or grain structure of wood veneers from a wood veneer surface in the way of its darkness (R). If the wood veneer comprises a number of local first regions, which are darker than a predominant darkness of the veneer surface, the wood veneer in question has its calculated dry substance density ($\rho_C$) established to be lower than its initially measured value ($\rho_M$). On the other hand, if the wood veneer has a substantially uniform darkness, the wood veneer in question has the longitudinal and lateral distribution of its dry substance density evaluated and, if those are substantially uniform, the calculated dry substance density ($\rho_C$) of the wood veneer in question is established for a sorting process to be higher than its initially measured value ($\rho_M$). Wood veneers are sorted on the basis of said calculated dry densities for at least two different density categories. In a first density category (A), the dry substance density is higher than in a second density category (B). Wood veneers are laid on top of each other for multi-layer wood, plywood, or some other sandwich material (20), the veneers included in the first density category serving as surface veneers (13) and the veneers included in the second density category serving as middle veneers (14).

35 Claims, 5 Drawing Sheets

ANALYZING AND SORTING OF WOOD VENEERS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The invention relates to a method for increasing strength and/or reducing strength variations in multi-layer wood, plywood, or the like sandwich material having a multiplicity of laminated wood veneers, said method comprising: measuring individual wood veneers for dry substance density, as well as for longitudinal and lateral distributions thereof, with high-frequency electromagnetic resonance; sorting wood veneers on the basis of said dry substance density for at least two different density categories, the dry substance density in a first density category being higher than in a second density category; laying wood veneers on top of each other for building multi-layer wood, plywood, and the like sandwich material consisting of a multiplicity of laminated wood veneers, such that veneers included in the first density category are placed as surface veneers, and veneers included in the second density category are placed as inner or middle veneers.

(2) Description of Related Art Including Information Disclosed Under 37 C.F.R. 1.97 and 1.98

U.S. Pat. No. 5,524,771 discloses a method of the above type, which has enabled a substantial increase in strength and at the same time a substantial reduction in strength variations in multi-layer wood, plywood, and the like materials consisting of a multiplicity of laminated wood veneers. A method and a sensor based on high-frequency electromagnetic resonance have been described in U.S. Pat. No. 4,739,249. It has been concluded, however, that although high-frequency electromagnetic resonance enables a high-speed and reliable measurement regarding dry substance density which represents strength and internal strength variations of wood veneers, and regarding longitudinal and lateral distributions of dry substance density, even that is not capable of detecting all flaws appearing in wood veneers, or the reason for a detected anomaly in density is not unambiguous, and thus cannot be applied as a basis for sorting. For example, knots contained in wood veneers, which also have an influence on the strength of a wood veneer, cannot generally be visualized by means of high-frequency electromagnetic resonance. Of course, the wood veneers containing knots can be detected and sorted visually, but such a manual inspection leads to a slower sorting of wood veneers and, especially when conducted in a hurry, is inaccurate and unreliable. In addition, it requires a highly skilled person to do it, prohibits automated sorting, and thus increases costs of sorting.

Another possibility of detecting knots is to apply ultrasonic measuring, a method and apparatus for this being described in the article: James D. Logan, "Machine Sorting of Wood Veneer for Structural LVL Applications"—34th International Particleboard/Composite Materials Symposium Proceedings, Apr. 4–6, 2000. However, an ultrasound apparatus may be an expensive investment and there are downsides, including first of all that a good contact must be established between an ultrasonic sensor and a wood veneer, which is very difficult when dealing with a dried and waving wood veneer, and that the temperature of a wood veneer has an impact on the measuring result. Eventual arrangements, in an attempt to eliminate some of the effects of temperature, increase costs even further. Secondly, it must be noted that ultrasonic measuring comprises at least one-time reading, i.e. a process which is indeed considerably slower than measuring performed with high-frequency electromagnetic resonance, and consequently, in an eventual combination of the above, the ultrasonic measuring constitutes a speed limiting factor and, thus, the sorting is not as fast and effective as it otherwise could be. A further drawback in ultrasonic measuring is the breakdown of wood veneers resulting from mechanical contact between a sensor applied therein and a wood veneer, whereby such veneers become useless.

BRIEF SUMMARY OF THE INVENTION

It is an object of the invention to provide such a method, whereby knots present in wood veneers and numbers thereof are detected at a speed at least equal to that used by high-frequency electromagnetic resonance to measure the dry substance density of a wood veneer. A second object of the invention is this type of method, which is adaptable for use in an automated sorting system for wood veneers. A third object of the invention is this type of method, which would be able to unambiguously reveal the cross-grain or slope of grain of a wood veneer, which, despite the fact that the wood veneer may have an averagely sufficient dry substance density, indicates a low veneer strength. A fourth object of the invention is this type of method, which would be implementable at reasonable costs both for new and existing wood veneer measuring and sorting mechanisms.

The foregoing drawbacks can be eliminated and the above objects can be achieved by a method of the invention, which comprises analyzing the homogeneity and/or grain structure of individual wood veneers from a large number of various points on a wood veneer surface on the basis of the optical reflectivity of said surface represented by its darkness; and when said optical reflectivity indicates in an individual wood veneer: I} a plurality of local first regions, which are substantially darker than a predominant darkness of the surface of a veneer/veneers, the calculated dry substance density value of the wood veneer in question is established for a sorting process to be lower than its initially measured value; or II} a substantially uniform darkness in comparison with the predominant darkness of a veneer surface, the longitudinal and lateral distribution of dry substance density in the wood veneer in question is evaluated, and, if those are essentially uniform, the calculated dry substance density value of the wood veneer in question is established for a sorting process to be higher than its initially measured value; as well as sorting the wood veneers on the basis of said calculated values for said at least two density categories of discontinuities and/or short gaps lengthwise of timber.

Benefits gained by a method of the invention include firstly that a measurement of wood veneer darkness, based on optical reflection, can be used for detecting knots present in a wood veneer and the location or distribution thereof in the veneer. If necessary, such inventive measuring can be readily used for detecting even very small knots by selecting a sufficiently high resolution for the employed detector system or camera. A second advantage offered by the invention is that the joint application of inventive measuring and a measurement with high-frequency electromagnetic resonance can be used for detecting e.g. possible cross-grain or slope of grain in a wood veneer. The cross-grain arises, as known, in a veneer, which is cut from a butt log having a butt end widening, or from a reaction wood log, generally described a cross-grain is caused by general or local curvature of the log. A third benefit gained by the invention is its feasibility for measuring the properties of all market-bound veneers without wastage, since measurements based both on high-frequency electromagnetic resonance and on the optical reflectivity of a veneer surface take place without a material/mechanical contact with wood veneers, which thus cannot be damaged as a result of inventive measurements and analyzation and, consequently, a truly non-destructive test method suitable for brittle and fragile wood veneers has now been developed. A fourth advantage of the invention is that the inventive measurements, i.e. measurements regarding the average rate and distribution of local darkness and dry substance density, and the sorting performed on the basis of such measurements shall result in multi-layer wood, plywood, or the like sandwich material consisting of a plurality of laminated wood veneers, having an average strength which is higher and a strength variation—i.e. a scatter or confidence interval in probabilistic terms—which is lower than in equivalent timber made from unsorted veneers, even if poor-quality veneers were not rejected or discarded in the sorting process. If the definitely poorest quality veneers—the number of which is generally relatively few and, thus, the rejection does not lead to an essentially reduced yield—are discarded according to further features of the invention in the manufacture of a relevant product, the strength can be increased and its variation reduced even considerably further. It is also conceivable to sort out wood veneers in view of manufacturing products of various strength categories. A fifth benefit offered by the invention is that the inventive calculated dry densities, established on the basis of darkness and dry substance density, can be applied for preventing cross-grained or slope-of-grain veneers from ending up in product surfaces or finishing layers. A further advantage of the invention is that the inventive measurement for the darkness of a wood veneer based on optical reflection, as well as integration of such measurement with a measurement performed with high-frequency electromagnetic resonance, are feasible by using commercially available equipment and, thus, the costs remain comparatively low. Still another benefit gained by the invention is that the inventive measurement for the darkness of a wood veneer based on optical reflection is feasible by means of a relatively lightweight and compact apparatus, whereby, for example, installation afterwards are possible in many cases.

BRIEF DESCRIPTION OF THE SEVERAL VIEWS OF THE DRAWINGS

The invention will now be described in detail with reference to the accompanying drawings.

DETAILED DESCRIPTION OF THE INVENTION

Figures 1, 2:
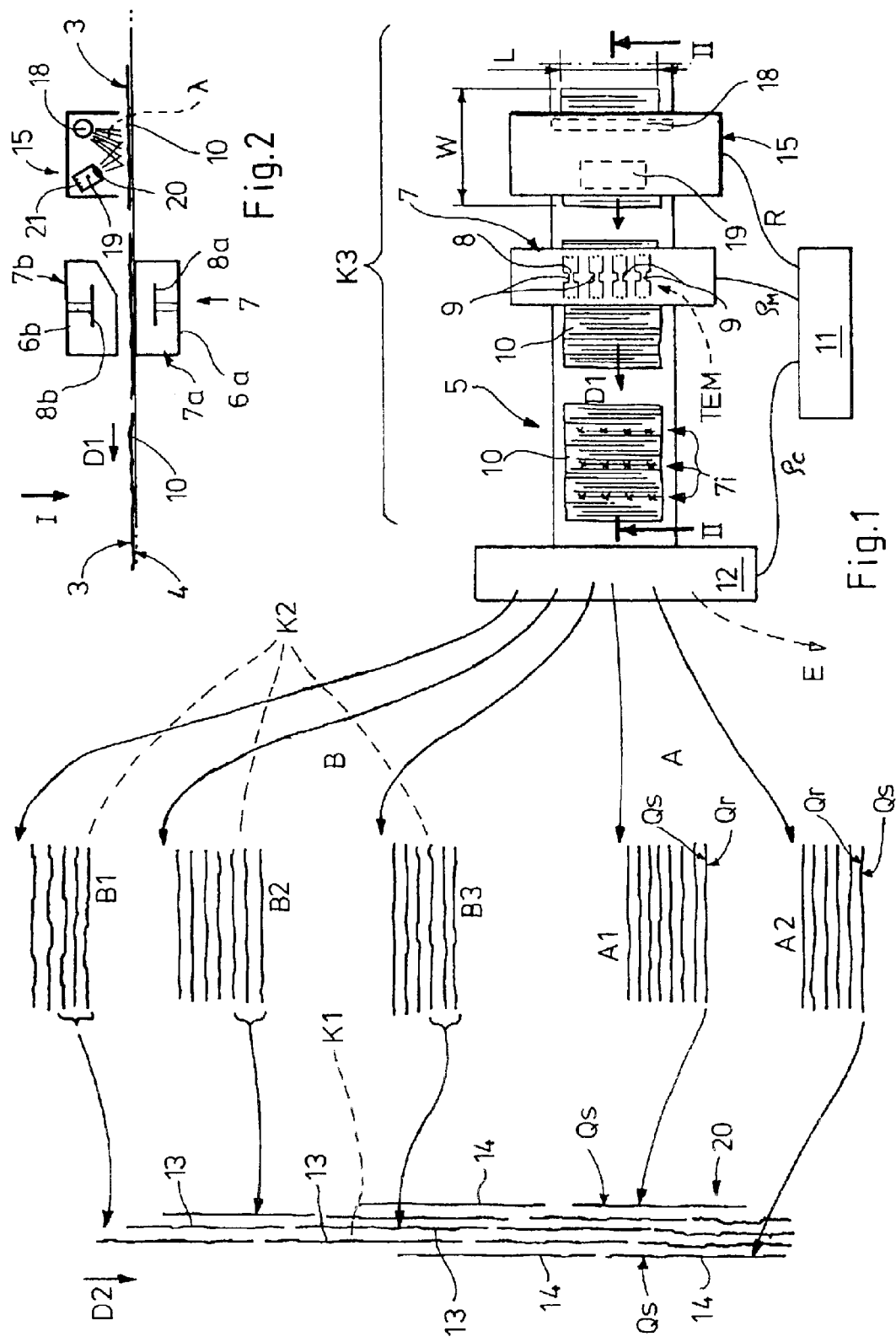
FIG. 1 shows schematically a production line of the invention, comprising equipment for measuring in a non-destructive manner the dry substance density of wood veneers and equipment for measuring in a non-destructive manner the knot density of veneers on a veneer line, as well as a sorting system for veneers, partially in a plan view from above the veneer line and partially in a lateral view from the direction I of FIG. 2.
FIG. 2 shows a veneer line in cross-section at said measuring equipment in a plane II—II of FIG. 1.

In view of increasing strength and/or reducing strength variations in multi-layer wood, plywood, and the like sandwich material consisting of a multiplicity of laminated wood veneers, the method comprises first of all measuring individual wood veneers 10, i.e. cut-to-size wood veneers, progressing along a conveyor track 5 in a direction D1, for a dry substance density $\rho$ as well as for longitudinal $\rho_{ML}$ and lateral distributions $\rho_{MW}$ of dry substance density with high-frequency electromagnetic resonance TEM. In this case, it is most preferable to use a highly developed type of quasi-TEM transmission-line resonator, wherein both inner conductors 8a, 8b located between ground planes 6a, 6b present both in a top section 7b and in a bottom section 7a of a resonator 7 and a veneer 10 existing roughly in the middle are designed as sensor elements controlled by p-i-n diodes 9. This type of configuration is described in the publication Vainikainen, Nyfors, Fischer: "Radiowave Sensor for Measuring the Properties of Dielectric Sheets: Application to Veneer Moisture Content and Mass per Unit Area Measurement"; IEEE Transactions on Instrumentation and Measurement, Vol. IM-36, No. 4, December 1987. Subsequently in this specification, reference is principally made to a type of sensor described in the above-cited publication, when dealing with a sensor for measuring dry substance density and, thus, strength. Hence, the configuration of this sensor is not explained in detail in this application. By means of a measuring sensor described in the above-cited reference, the dry total mass of a product per unit area can be calculated from a resonance frequency or a quality factor given by the sensor. As well known in the art, these are in turn dependent on the real portion and imaginary portion of a veneer's dielectric constant. Since the resonator 7 comprises a number of p-i-n diodes 9, i.e. individual resonators 9 side by side in a line transverse to the advancing direction D1, and since the wood veneers to be measured travel during a measuring process in the direction D1, the wood veneers shall reveal the above-mentioned longitudinal distributions $\rho_{ML}$ and lateral distributions $\rho_{MW}$ of dry substance density, i.e. a large number of measuring points 7$i$, which are distributed across a veneer length L and width W and visualized by way of example with crosses x in FIG. 1. In this specification, the veneer length L represents the principal grain direction of a veneer and coincides with the longitudinal direction of a tree trunk from which the veneer is rotary cut, whereas the veneer width W is a dimension perpendicular to the length. Dry substance density refers to a volume weight, e.g. kg/m$^3$, after the elimination of moisture contained in a wood veneer, i.e. its water content, so dry substance density represents the presently wood veneer in question in a hypothetical, totally dry state.

The above-mentioned quasi-TEM transmission-line resonator 7 is connected for example to a computer 11, to which dry densities and other measured quantities are transferred and stored for performing required calculations and for compiling control quantities for a sorting process. The computer 11 is further connected to a sorter 12 which, on the basis of control quantities received from the computer, distributes each wood veneer 10 on the basis of its dry substance density to at least two categories A and B, such as, for example, for two stacks of veneers. The sorter 12 can be of any prior known or novel construction and, thus, shall not be described here in more detail. On the basis of dry densities thereof, measured as described above, the wood veneers are sorted for at least two different density categories, the first density category A exhibiting a dry substance density and, thus, also a strength higher than those existing in the second density category B, the veneers being sorted into the latter having a dry substance density and, hence a strength lower than those existing in the first density category A. This is followed by stacking or piling the sorted wood veneers in any convenient prior known or novel manner on top of each other for multi-layer wood, plywood, and a corresponding sandwich material 20 consisting of a multiplicity of laminated wood veneers. The veneers included in this first density category A are placed or organized as surface veneers 14 and the veneers included in the second density category B are placed or organized as inner veneers or middle veneers 13, in other words between the surface veneers 14, as described for example in the Applicant's earlier patent U.S. Pat. No. 5,524,771.

According to the invention, the method further comprises analyzing the homogeneity and/or grain structure of individual wood veneers 10 from a large number of various points along the surface of a wood veneer or veneer sheet. This homogeneity of wood veneers is measured on the basis of optical reflectivity manifesting itself in the form of darkness R of at least one surface 3 or 4. The optical reflectivity R of a wood veneer is measured by illuminating one 3 of the two wood veneer surfaces 3, 4 by means of an appropriate light source 18, such as an electric lamp, by exposing the thus illuminated surface to a camera 19, which has a lens 20 and either a line element 20 or a area element 21, i.e. an array of detectors, as a photosensitive element, the light radiation reflected thereto from said wood veneer surface 3 transforming to electrical signals which are proportional to received quantities of light. A measurement for the optical reflectivity R of a wood veneer for said analyzing is performed by using light or electromagnetic radiation, having its wavelength $\lambda$ within an ultraviolet range or a visible range or an infrared range. When a measurement for the optical reflectivity of a wood veneer is effected by means of a line-element equipped camera, its line of detectors is set in a position transverse to the wood veneer advancing direction D1, whereby the veneer advancement in the direction D1 produces measuring results across a veneer dimension co-directional therewith. Similarly, an area-element equipped camera is capable of utilizing a veneer movement, or the camera can be focused for taking a picture of the entire veneer at one time. Such cameras 19 are commercially available in several different types and, hence, shall not be described here in more detail. The light source 18 and the darkness measuring camera 19 constitute an artificial vision unit 15, which is connected for example to the computer 11, to which the individual measured values or darkness values received from the camera 19 are transferred and stored for performing required calculations and for compiling control quantities for a sorting process. In view of said analyzing, the darkness values are measured over the entire wood veneer length L and width W, with the camera 19 having such a resolution that is capable of producing a sufficiently detailed image and darkness values of the wood veneer surface for identifying eventual knots, whereby there is available a large number of darkness values to be optimally maintained as an almost continuously varying value and picked up from various points of the veneer surface.

These darkness values can then be searched with an appropriate computer program for finding points or regions different in terms of their reflectivity or darkness R and for feeding the same for further processing. This application is not directed to computer programs, which is why the analyzing program for images is not described in more detail. For further analyses, however, either the surface of each veneer can be used for calculating a predominant darkness $\overline{R}$, i.e. an average or mean darkness, or a predetermined number of veneers used for calculating a fixed or variable predominant darkness $\overline{R}$. The calculation of averages is effected by means of commonly known mathematical methods, which thus need not be further described in this context. A useful reference point may also be provided by the predominant darkness $\overline{R}$, which is predetermined and stored in the memory of a computer. On the other hand, the values $\rho_M$, initially measured as dry substance density of the individual wood veneers 10, are the average or mean values $\overline{\rho}$ of each individual wood veneer 10 measured on the basis of signals received respectively with the above-mentioned high-frequency electromagnetic resonance, i.e. $\rho_M = \overline{\rho}$. The calculation of these averages of dry densities is likewise effected by commonly known mathematical methods, which, therefore, need not be described in this specification.

Figure 5:
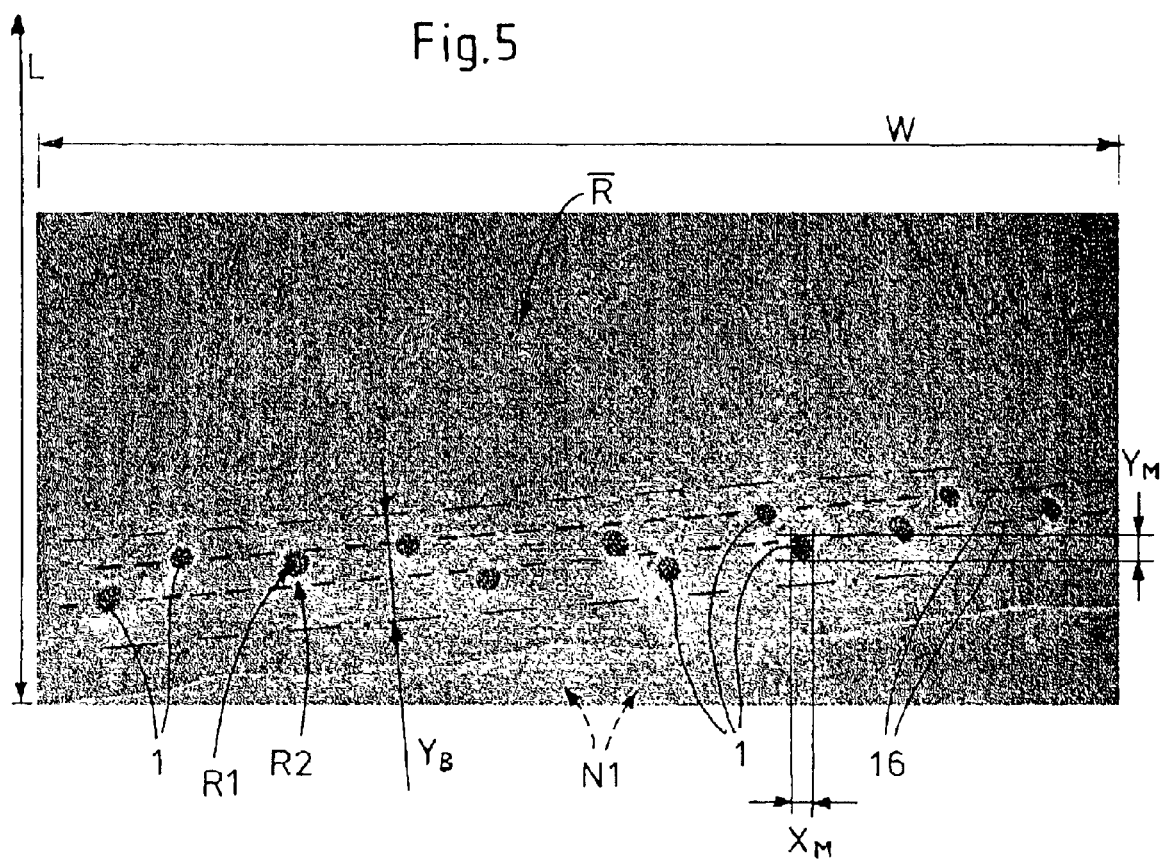
FIG. 5 depicts the appearance of a knotty wood veneer, which is measured with a knot-detecting device mounted on the veneer line.

When the optical reflectivity or darkness value, mentioned above and measured from the wood veneer surface 3 or 4, indicates in a single wood veneer 10 a plural number N1 of local first regions 1, which are substantially darker R1 than the predominant darkness $\overline{R}$ of the surface of a veneer/veneers, the calculated dry substance density $\rho_C$ of this particular wood veneer is established for a sorting process to be lower than its initially measured value $\rho_M$, for example by a predetermined amount $^-\Delta 1$ lower than its initially measured average value $\rho_M$. FIG. 5 visualizes some first regions 1 or knots, the number N1 of which in this case is twelve. In many cases the first regions 1 are surrounded by a narrow belt, having a darkness, which is lesser R2 than the predominant darkness $\overline{R}$, as depicted in FIG. 5, which may sometimes facilitate identification of the first regions. Typically, however, the first local regions 1 are evaluated to comprise areas, whose length $Y_M$ and/or width $X_M$ exceed predetermined dimensions $Y_\rho$, $X_\rho$, and whose darkness R is at least by a predetermined amount $R_A$ more intense than either the average darkness measured from veneers of this particular variety of wood or the average darkness $\overline{R}$ of a particular individual veneer. This is especially true if there is a small relative difference between the first regions and the predominant darkness. The characteristics of the first regions are at least to some degree specific to a species of wood and, thus, for the identification thereof, the computer 11 must be programmed to possess appropriate reference values. Especially, when the first local regions are spread out, i.e. not in a row or rows 16, and fewer in number than a preset number M1, the calculated dry substance density $\rho_C$ can be established to be by the above-mentioned first amount $^-\Delta 1$ lower than its initially measured average value $\rho_M$. On the other hand, when the first local regions 1 constitute a row or rows 16 substantially transverse to the wood veneer length L, the calculated dry substance density $\rho_C$ can be established to be by a predetermined third amount $^-\Delta 3$ lower than its initially measured average value $\rho_M$. In terms of its absolute value, this third amount $^-\Delta 3$ exceeds the first amount $^-\Delta 1$ and, thus, provides a further reduction of dry substance density. A row is considered to be present when there are at least three first local regions 1 within a predetermined bandwidth $Y_B$. Transversal means here that the longitudinal direction of the bandwidth forms an angle smaller than 45°, in most cases smaller than 30°, in respect to the main grain of the veneer sheet, whereupon the direction main grain respect to the veneer length L and the length of the log.

Figure 3:
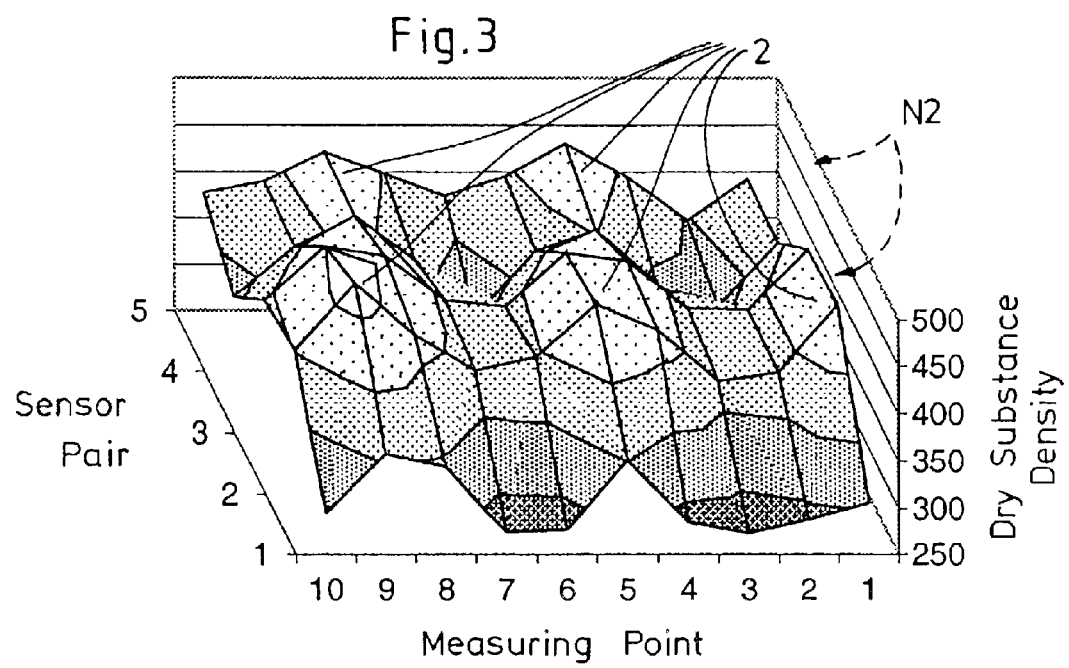
FIGS. 3 and 4 depict by way of example the distribution of dry substance density in cross-grained and high-quality wood veneers, respectively, over a section of the total surface area of a single wood veneer.
Figure 4:
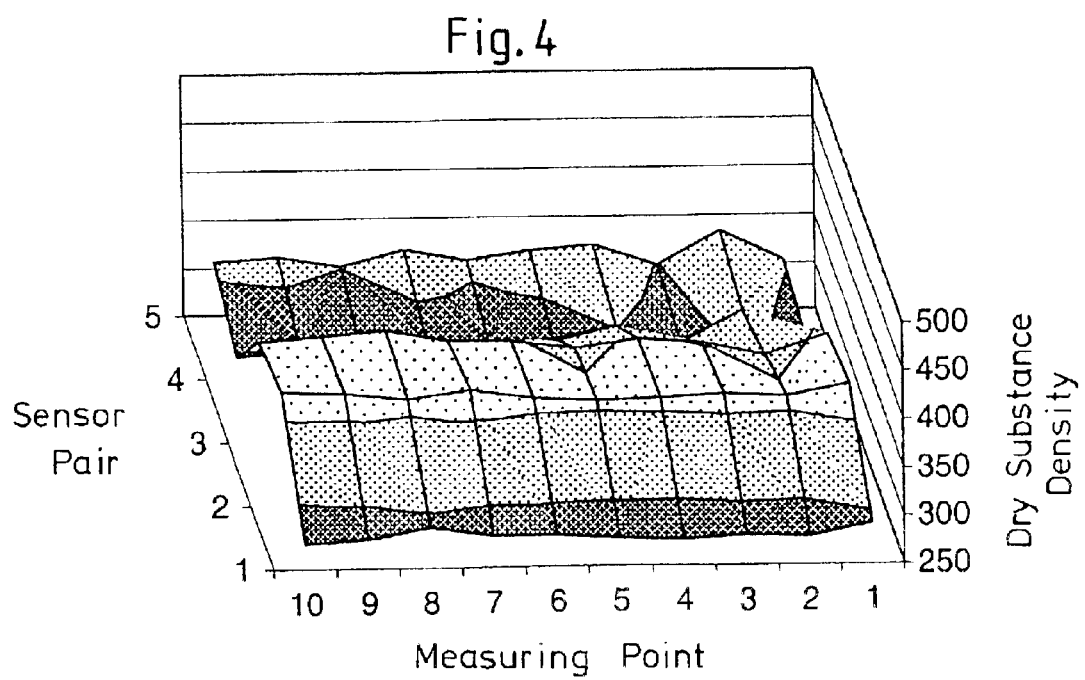

On the other hand, if the optical reflectivity or darkness value measured from the wood veneer surface 3 or 4 indicates in a single wood veneer 10 a substantially uniform darkness as compared with the predominant darkness $\overline{R}$ of the veneer surface, this is followed by studying the longitudinal and lateral distribution of dry substance density in this particular wood veneer. A first alternative detection: when the longitudinal and lateral distributions $\rho_{ML}$, $\rho_{MW}$ of dry substance density in a particular wood veneer are substantially or to a predetermined degree uniform, i.e. the difference from the average initially measured dry substance density $\rho_M$ is lower than a predetermined limit value $\rho_A$, the calculated dry substance density $\rho_C$ of this particular wood veneer is established for a sorting process to be higher than its initially measured value $\rho_M$, for example by a predetermined fourth amount $^+\Delta 4$ higher than its initially measured average value $\rho_M$. FIG. 4 visualizes such a sufficiently even or uniform distribution of dry substance density. A second alternative detection: when the longitudinal and lateral distributions $\rho_{ML}$, $\rho_{MW}$ of dry substance density in a particular wood veneer comprises a plural number N2, such as more than a predetermined number M2, of discrete second regions 2, wherein the dry substance density $\rho_{MP}$ is essentially higher than in a region $\rho_{MO}$ surrounding the same, the calculated dry substance density $\rho_C$ of this particular wood veneer 10 is established for a sorting process to be lower than its initially measured value $\rho_M$, for example by a predetermined second amount $^-\Delta 2$ lower than its initially measured average value $\rho_M$. FIG. 3 visualizes such a dry substance density distribution, comprising this type of second regions 2.

According to the inventive principle, the wood veneers 10, i.e. discrete veneer sheets of a given size, are then sorted out on the basis of their calculated dry densities $\rho_C$ for said at least two density categories A, B. Thus, the sorting of wood veneers is performed by reducing or increasing the initially measured dry substance density value $\rho_M$, or in some cases without changing the initially measured value $\rho_M$, in any case first producing a calculated dry substance density $\rho_C$ and performing the sorting only on the basis of this calculated value, not on the basis of the original measured value. Hence, the fact that the sorting is always performed on the basis of the calculated dry substance density $\rho_C$ does not exclude the possibility that the calculated dry substance density could be equal to the measured dry substance density, although in most cases these are unequal for a sorting process. Thus, sorted for the first density category A are those wood veneers, whose calculated dry substance density $\rho_C$ is higher than a predetermined first limit value $\rho 1$, and sorted for the second density category B are those wood veneers, whose calculated dry substance density $\rho_C$ is lower than a predetermined second limit value $\rho 2$. In this case, the second limit value is higher than or equal to a third limit value.

The density categories include generally also a zero category E, the calculated dry substance density $\rho_C$ of wood veneers to be sorted therefore being lower than a predetermined fifth limit value $\rho 5$. The wood veneers included in this zero category E are discarded from the manufacturing process of the present type of multi-layer wood, plywood, or the like sandwich material 20 consisting of a multiplicity of wood veneers. Of course, wood veneers bound for the zero category E can be used for some other purpose. Furthermore, the density categories may include a third category $A^+$, the dry substance density $\rho_C$ of wood veneers to be sorted therefore being higher than a predetermined third limit value $\rho 3$ and having none of the above-described first regions 1, nor second regions 2, and/or a fourth category $B^-$, the dry substance density of wood veneers to be sorted therefore being lower than a predetermined fourth limit value $\rho 4$ and having a higher number of the first regions and/or second regions than a given number M1. Regarding the above-described limit values, the following applies. The possible third limit value $\rho 3$ is higher than the first limit value $\rho 1$. The possible fourth limit value $\rho 4$ is lower than the second limit value $\rho 2$. The possible fifth limit value $\rho 5$ is lower than the second limit $\rho 2$ value and lower than the possible fourth limit value $\rho 4$. It should be appreciated that, in addition to the above-mentioned first and second categories A, B, other categories possibly selected for sorting wood veneers therein are decided on the basis of a generally known quality standard for products to be manufactured and veneers to be sorted. Likewise, the above-mentioned limit values $\rho 1-\rho 5$ and dry substance density varying amounts $^+\Delta 4$ and/or $^-\Delta 1$ and/or $^-\Delta 2$ and/or $^-\Delta 3$ are chosen in a similar fashion, as warranted by the situation. It should further be noted that, as calculated dry densities $\rho_C$ for a sorting operation, it is also possible to apply the relative values thereof and, thus, even though it is a preferred objective, there is no compelling reason for attempting to simulate the truly effective value thereof, which would be consistent with the real strength. It is because of the relativity that any of the varying amounts $^+\Delta 4$, $^-\Delta 1$, $^-\Delta 2$, $^-\Delta 3$ of dry substance density can be chosen to be for example zero or some other value, as long as the limit values $\rho 1-\rho 5$ for categorization are chosen in a corresponding manner for a desired sorting result. So the relatively lower and higher calculated dry substance density values ($\rho_C$) of the wood veneers can actually be lower and respectively higher than or equal with the initially measured values ($\rho_M$). This alternative means that calculated dry substance density values, corrected to correspond their effect on the strength of the veneers are used for the sorting. This is the preferred way of operation. Alternatively the relatively lower and higher calculated dry substance density values ($\rho_C$) can have lower and respectively higher or equal virtual values, which are modified from the initially measured values ($\rho_M$) to a direction of higher values or lower values while maintaining the calculated and changed or corrected difference between them. This latter alternative means that calculated dry substance density values, which, in a mathematical sense, are transferred parallel along the dry substance density axis and which makes them artificial values not directly describing strength, are used for the sorting. In spite of said virtuality, sorting to correct categories is possible. But, as stated above, it is nevertheless appropriate to design these varying amounts and limit values to be as highly consistent as possible with their impact on strength.

The above-discussed second category B is intended for the innermost veneer layers of multi-layer wood, plywood, and the like sandwich material 20 consisting of a multiplicity of laminated wood veneers. More specifically, for inner veneers 13 there is a single category of veneers, i.e. the second category B, the veneers included therein being nevertheless sorted for at least two veneer stacks B1 and B2, but in most cases, preferably for three or more veneer stacks B1, B2, B3 etc., which function as buffer stocks in the manufacture of multi-layer wood, plywood, and the like sandwich material. In these separate staples or stacks B1, B2, B3 included in the second category, the predetermined average values $\overline{\rho}_{PB}$ of calculated dry substance density are identical to each other. According to the invention, a single wood veneer 10 sorted for this second category B will be placed in that particular one of the veneer stacks in which it changes the moving average $\overline{\rho}_{CB1}$ or $\overline{\rho}_{CB2}$ or $\overline{\rho}_{CB3}$ of calculated dry densities in this particular stack by the largest amount towards the predetermined average $\overline{\rho}_{PB}$. Simply put, this means that if, for example in plywood designed to include three middle veneers, the dry substance density and strength of one veneer are very low, the other two veneers to be set in alignment therewith must have reasonably high dry densities or one of these must have a particularly high dry substance density, such that the average density and, hence strength, of these three veneers would be the same as the density of all middle veneers on average. In the described system, used for upholding the moving averages of dry densities in several veneer stacks, the average of densities in correspondingly laminated middle veneers 13 can be maintained consistent along the length of multi-layer wood, i.e. in its laying direction D2. The procedure is particularly such that, if the sorted wood veneers are supplied onto veneer stacks from above, the veneer is picked up as a group G of a given size from each veneer stack B1, B2, B3. The number of wood veneers included in this group G can be equal to or lower than a number K1 of middle veneers for multi-layer wood, plywood, and the like sandwich material. The number of wood veneers 10, which is taken into account in the calculation of a moving average, is proportioned to the number of middle veneers 13 included in the thickness of multi-layer wood, plywood, and the like sandwich material, and it is typically from five to twenty-five. Since the veneers cut from a single tree trunk have dry densities of the same order, although often not exactly the same—the difference between dry densities of veneers cut from the surface portions or core portions of a tree trunk depends e.g. on a species of wood—and since the cutting process of veneers may be supplied in succession with two or even more logs of a similar type of wood, the result can be a comparatively large number of wood veneers with roughly the same dry substance density and, thus, strength. If the category regarding a particular dry substance density only contains a small number of veneer stacks and the product 20 to be manufactured, i.e. multi-layer wood, plywood, and the like sandwich material, is made by using just a small number, such as three or four, of middle veneers 13 for example, it may happen that the variations of dry substance density cannot be properly compensated for. Accordingly, a number K2 of veneer stacks—in the foregoing example the number K2 of stacks is three—must also be chosen to be appropriate or sufficient as proportioned to the number of middle veneers 13 included in the thickness of multi-layer wood, plywood, and the like sandwich material, as well as possibly to a number K3 of wood veneers to be cut from each log. Presumably, it is preferred that the number of veneer stacks be at least equal to the number of wood veneers or veneer sheets to be averagely cut from a single tree trunk, divided by the number of middle veneers or the like to be used for the product, i.e. $K2 \geq K3/K1$. Thus, it would also be possible to reduce the number of wood veneers/veneer sheets considered in the calculation of a stack-specific moving average to be equal to the number K1 of wood veneers, for example middle veneers, intended for a certain location in the product, or to be close to the number K1 of (middle) veneers. It is then likewise possible to set the groups G picked up from veneer stacks to be equal in number to the number K1 of wood veneers, for example middle veneers, intended for a certain location in the product, or to be close to the number K1 of (middle) veneers, thus resulting in G=K1. Of course, it is also conceivable to choose the above-mentioned groups and the numbers of veneer stacks in some other way. It should be appreciated that what has been said about middle or inner veneers applies to any other category of wood veneers, as well. It is of course possible to use a slightly larger number of veneers or a slightly smaller number of veneers as a calculation basis for moving average. In addition, each of these veneers included in calculation can be provided with an equal or unequal weighted value in the calculation of average. Since the veneer sheets, for example in plywood and multi-layer wood, are slightly overlapped as visualized in FIG. 1, the veneers are not always in practice picked up for example three at a time but, instead, three in succession at short intervals, followed by moving over to the next stack, from which the same number of veneers are also picked up at short intervals. Another possibility is to supply a continuous web of veneer as such, cut from a tree trunk, to the measurement of dry substance density and surface darkness, performed according to the invention as described above, and to finally cut the veneer strip on the basis of the calculated dry densities $\overline{\rho}_C$ obtained from its various regions for veneer sheets or separate wood veneers included in various categories. Hence, it is perhaps possible to separate high-quality regions from poor-quality regions in a veneer strip.

The above-described first category A is intended for an outermost veneer layer or outermost veneer layers 14, i.e. surface veneers, in multi-layer wood, plywood, and the like sandwich material 20 consisting of a multiplicity of laminated wood veneers. As described above, veneers included in this single category A can be sorted for one or more veneer stacks A1, A2. Thus, the wood veneers 10 sorted out for this first category A are used to maintain the moving average $\overline{\rho}_{CA1}$, or $\overline{\rho}_{CA2}$ of calculated dry substance density/dry densities in each veneer stack/veneer stacks so as to remain at or above an average $\overline{\rho}_{PA}$ predetermined for this category, by bringing each wood veneer to that particular one of the stacks, in which it changes the moving average $\overline{\rho}_{CA1}$ or $\overline{\rho}_{CA2}$ of calculated dry densities in this particular stack by the largest amount towards the predetermined average $\overline{\rho}_{PA}$. In this case as well, the veneer stack A1 or the veneer stacks A1, A2 function as a buffer stock. This control of a moving average by means of several veneer stacks has significance, even in the case that just a single surface veneer were used for multi-layer wood, plywood, and the like sandwich material 20 to be manufactured on each external surface thereof for the reason that wood veneers cut from logs have different outer surfaces, whereby the surface veneers 14 to be applied as the outermost veneers in the product must be placed in such a way that their compact and smooth surfaces Qs face outward and rough surfaces Qr are set against the middle veneers 13 of multi-layer wood, plywood, and the like sandwich material 20. In theory, the first category A could be comprised of just one veneer stack and veneers picked up therefrom could be turned right side up for a laying process, but this would incur more equipment costs and a risk of breaking the brittle wood veneers. Therefore, it is appropriate to provide at least two veneer stacks A1 and A2 also for the first category used as surface veneers 14.

Generally, it can be said that wood veneers heading for each different category $A^+$, A, B, $B^-$ are mutually organized in such a way that their dry densities have moving averages $\bar{\rho}_{CA+}, \bar{\rho}_{CA}, \bar{\rho}_{CB}, \bar{\rho}_{CB-}$ which converge continuously towards an average $\bar{\rho}_{PA+}, \bar{\rho}_{PA}, \bar{\rho}_{PB}, \bar{\rho}_{PB-}$ predetermined for this particular category, when using the previously determined category definitions as lower indices to represent the properties of these particular categories.

Figure 6:
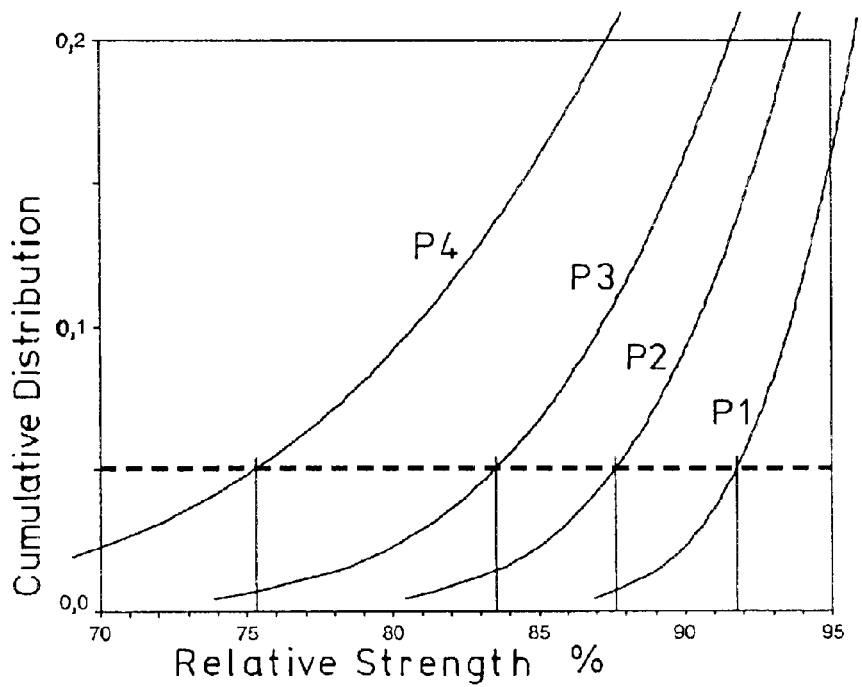
FIG. 6 illustrates statistically the probabilistic strength distributions in pieces of finished plywood, multi-layer wood, and the like sandwich materials consisting of a multiplicity of laminated wood veneers, more particularly the cumulative distributions or summed functions of relative strengths, comprising the relative strengths of sandwich materials produced by unsorted wood veneers, those of sandwich materials produced by wood veneers sorted solely on the basis of dry substance density, as well as the relative strengths of sandwich materials produced by wood veneers sorted according to the invention, in practice and in a theoretically calculated form.
Figure 7A:
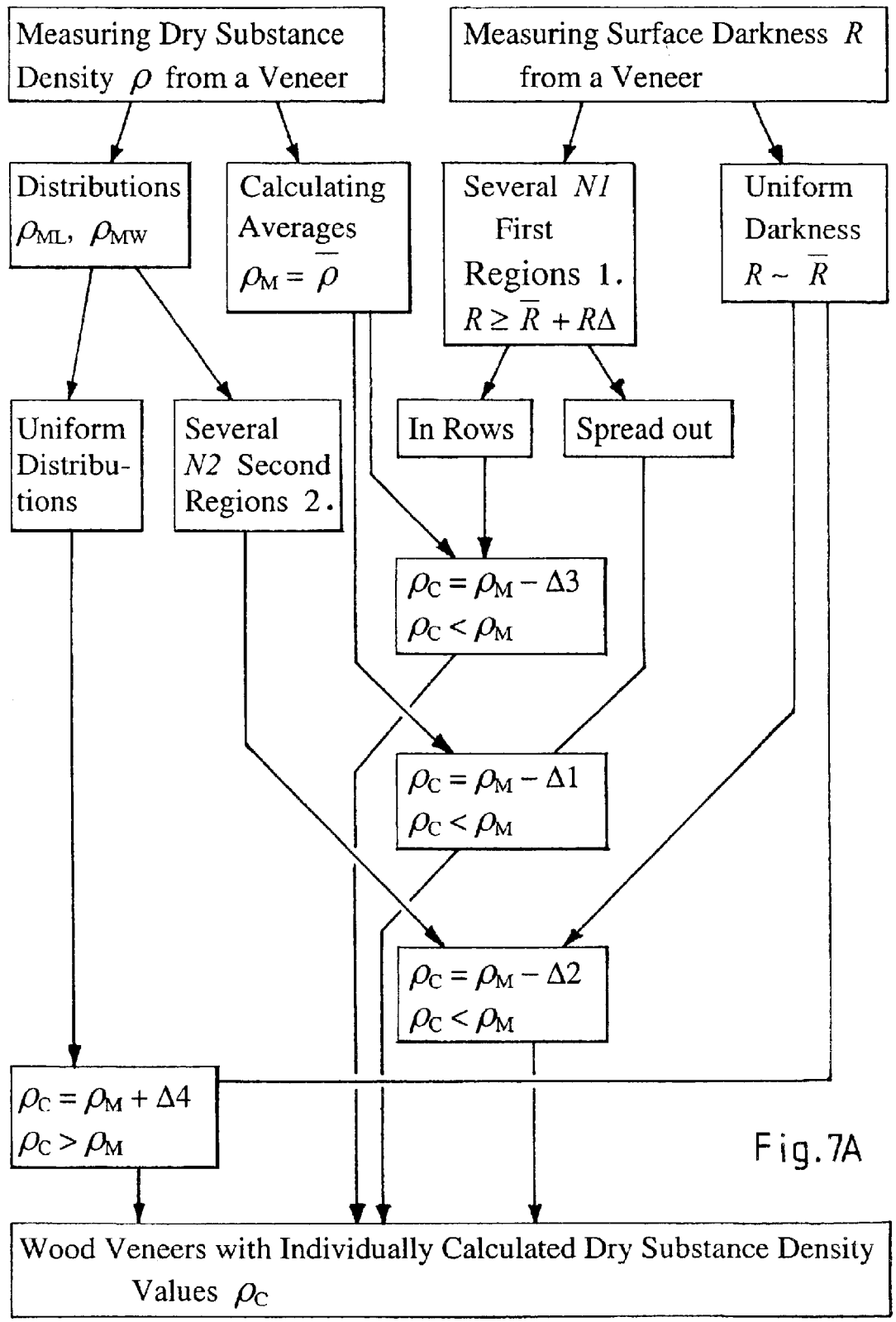
FIG. 7A shows a diagram for that part of a method of the invention, in which the measured dry densities of wood veneers are deduced to calculated dry densities on the basis of measurements conducted on each wood veneer.
Figure 7B:
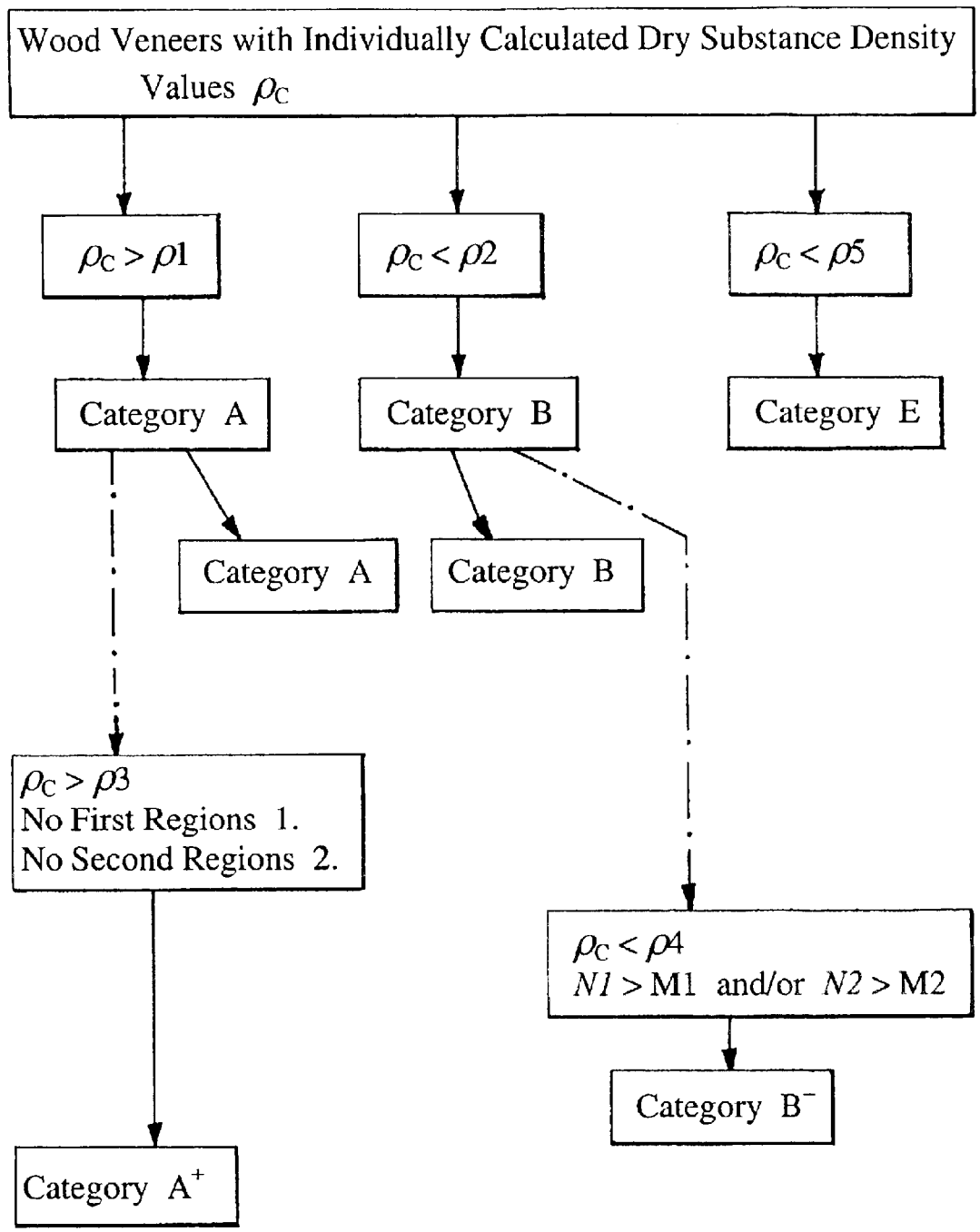
FIG. 7B shows a diagram for that part of a method of the invention, in which wood veneers are sorted for different categories on the basis of calculated dry densities based on measurements.

Regarding the strength and strength variations of multi-layer wood, plywood, and the like sandwich material 20 manufactured by using wood veneers sorted in various ways and unsorted wood veneers, it can be appreciated that the inventive method enables both increasing average strength and reducing statistical scattering. In FIG. 6, the horizontal dashed line is used to demonstrate an appearance frequency of 5% (=0.05), i.e. 95% of sandwich material products have strength, which is higher than the value at this point. A curve P4 demonstrates the relative strength of such sandwich materials 20 which are made of unsorted wood veneers, i.e. various wood veneers contained in such sandwich materials are located haphazardly. In that case, the relative strength is about 75% of the average strength $\bar{X}_4$ of such products, and a so-called characteristic strength $X=\bar{X}_4-1,645\times S_4$ with a certain species of wood in the order of 45 N/mm². Current manufacturing lines in normal production turn out products consistent with the curve P4. A curve P3 demonstrates a relative strength for such sandwich materials 20 which are manufactured from wood veneers sorted solely on the basis of dry substance density, by organizing veneers with a higher dry substance density on the surface of the sandwich material and veneers with a lower dry substance density in the middle of the sandwich material and by additionally controlling a moving average of dry substance density in the stack(s) of surface veneers and in several stacks of middle veneers, as described in the Applicant's earlier patent U.S. Pat. No. 5,524,771. In this case, the relative strength is about 84% of the average strength $\bar{X}_3$ of such products, and the so-called characteristic strength $X_{kar}=\bar{X}_3-1,645\times S_3$ with the same given species of wood is in the order of 50 N/mm². Curves P2 and P1 represent a relative strength for such sandwich materials 20 which are manufactured according to the invention, by applying a sorting process based on both dry substance density measured from wood veneers and its distributions and on measured darkness inconsistencies in the surface of wood veneers, in other words, manufactured from wood veneers sorted on the basis of calculated dry densities $\rho_C$ by organizing veneers with a higher calculated dry substance density on the surface of the sandwich material and veneers with a lower calculated dry substance density in the middle of the sandwich material, as well as by also controlling moving averages of calculated dry densities, e.g. $\bar{\rho}_{CB1}, \bar{\rho}_{CB2}, \bar{\rho}_{CB3}$ and $\bar{\rho}_{CA1}, \bar{\rho}_{CA2}$, in stacks of surface veneers and in several stacks of middle veneers, in accordance with this invention. In this case, it is theoretically possible to reach a relative strength of about 92% of the average strength $\bar{X}_1$ of the products in question, whereby the characteristic strength $X_{kar}=\bar{X}_1-1,645\times S_1$ with the same given species of wood would be in the order of 55 N/mm². Practice shows that it is quite easy to reach a relative strength of about 88% of the average strength $\bar{X}_2$ of the products in question while the characteristic strength $X_{kar}=\bar{X}_2-1,645\times S_2$ with the same given species of wood is in the order of 53 N/mm². In the above equations representing characteristic strength, quantities $S_1-S_4$ represent statistical scattering. It should be noted that all the above-described values, as well as the curves in FIG. 6, only illustrate a single example, and must neither be regarded as limiting the invention, nor limiting the benefits obtainable by the invention.

What is claimed is:

1. A method for increasing strength and/or reducing strength variations in multilayer wood, plywood, or sandwich materials having a plurality of wood veneers, one on the other, said method comprising the steps of:

measuring dry substance density, as well as longitudinal and lateral distributions of individual wood veneers, with a high-frequency electromagnetic resonance;

analyzing homogeneity and/or grain structure of the individual wood veneers from a large number of various points on a wood veneer surface on the basis of optical reflectivity of said surface represented by its darkness;

when said optical reflectivity indicates in the individual wood veneer:

I} a plurality of local first regions, which are substantially darker than a predominant darkness of the veneer/veneers surface, establishing a calculated dry substance density value of the wood veneer in question for the sorting process to be relatively lower than its initially measured value; or II} a substantially uniform darkness in comparison with the predominant darkness of the veneer/veneers surface, evaluating the longitudinal and lateral distribution of dry substance density in the wood veneer in question, and, if those are substantially uniform, establishing a calculated dry substance density of the wood veneer in question for a sorting process to be relatively higher than its initially measured value;

sorting the wood veneers on the basis of said calculated dry substance densities for at least two different density categories, the dry substance density in a first density category being higher than in a second density category; and laying wood veneers on top of each other for building said multi-layer wood, plywood, or sandwich material, such that veneers graded in the first density category are placed as surface veneers, and veneers graded in the second density category are placed as central veneers.

2. A method as set forth in claim 1, wherein the values initially measured for dry substance density of the discrete wood veneers are average values for each individual veneer, calculated on the basis of signals obtained by high-frequency electromagnetic resonance, which are reduced or increased or not changed for providing said calculated dry substance densities for the sorting process.

3. A method as set forth in claim 1, wherein, when the optical reflectivity indicates in a single wood veneer said plurality of the local first regions, the calculated dry substance density of this particular wood veneer is established for the sorting process to be by a predetermined relative first amount lower than its initially measured average value.

4. A method as set forth in claim 1, wherein, when said optical reflectivity indicates in a single wood veneer a substantially uniform darkness with respect to the predominant darkness of the veneer surface, evaluating the longitudinal and lateral distributions of dry substance density in the wood veneer in question; and when it contains a number of discrete second regions, having a dry substance density which is substantially higher than that in a surrounding area, establishing the calculated dry substance density of the wood veneer in question for a sorting process to be relatively lower than its initially measured average value.

5. A method as set forth in claim 4, wherein, when the longitudinal and lateral distributions of dry substance density in a particular wood veneer contain discrete second regions, whose number in the wood veneer in its longitudinal direction exceeds a predetermined number, and in which the dry substance density is substantially higher than in the surrounding area, the calculated dry substance density of the wood veneer in question is established for a sorting process to be by a predetermined relative second amount lower than its initially measured average value.

6. A method as set forth in claim 1, wherein, when said first local regions:
   are spread out and the number thereof is fewer than a preset number, the calculated dry substance density is established to be by a predetermined relative first amount Lower than its initially measured average value; and
   establish a row or rows transverse to a wood veneer length, the calculated dry substance density is established to be by a predetermined relative third amount lower than its initially measured average value.

7. A method as set forth in claim 1, wherein, when said optical reflectivity indicates a substantially uniform darkness and when the longitudinal and lateral distributions of the dry substance density are to a predetermined degree uniform in a particular wood veneer, the calculated dry substance density of the veneer is established to be by a predetermined relative fourth amount higher than its initially measured average value.

8. A method as set forth in claim 1, wherein wood veneers whose calculated dry substance density is higher than a predetermined first limit value are sorted for the first density category, and wood veneer whose calculated dry substance density is lower than a predetermined second limit value are sorted for the second density category.

9. A method as set forth in claim 8, wherein the second limit value is higher than or equal to a third limit value.

10. A method as set forth in claim 6, wherein wood veneers whose calculated dry substance density is higher than a predetermined first limit value are sorted for the first density category, and wood veneers whose calculated dry substance density is lower than a predetermined second limit value are sorted for the second density category.

11. A method as set forth in claim 10, wherein the second limit value is higher than or equal to a third limit value.

12. A method as set forth in claim 1, wherein said local first regions are defined to comprise areas, whose:
   length and/or width exceed predetermined dimensions, and
   darkness is by at least a predetermined degree more intense than either an average darkness calculated from veneers of a particular species of wood or an average darkness of a particular single veneer.

13. A method as set forth in claim 1, wherein for the central veneer layers of said multi-layer wood, plywood, or sandwich material one said second category is provided, the veneers included therein being sorted for at least two veneer stacks, in which the calculated dry substance density has predetermined averages which are identical to each other.

14. A method as set forth in claim 13, wherein a single wood veneer sorted for said second category is delivered into that of the veneer stacks, in which it changes a moving average of the calculated dry densities of the stack most towards the predetermined average.

15. A method as set forth in claim 1, wherein for the outermost veneer layer or veneer layers of said multi-layer wood, plywood, or sandwich material one said first category is provided, the veneers included therein being sorted for one or several veneer stacks.

16. A method as set forth in claim 15, wherein the wood veneers sorted for said first category are used for maintaining a moving average of the calculated dry substance density/densities of veneer stack(s) so as to remain at or above the average value predetermined for this category.

17. A method as set forth in claim 1, wherein the density categories include a zero category, the wood veneers to be sorted therein having a dry substance density which is lower than a predetermined fifth limit value.

18. A method as set forth in claim 17, wherein the wood veneers included in said zero category are discarded from the manufacturing process for the respective type of said multi-layer wood, plywood, and sandwich material.

19. A method as set forth in claim 8, wherein the density categories include a third category, the wood veneers to be sorted therein having a calculated dry substance density which is higher than a predetermined third limit value and having none of the first regions nor second regions.

20. A method as set forth in claim 8, wherein the density categories include a fourth category, the wood veneers to be sorted therein having a calculated dry substance density which is lower than a predetermined fourth limit value and having a number of the first regions and/or second regions in excess of a given number.

21. A method as set forth in claims 8 and 9, wherein the optional third limit value is higher than the first limit value.

22. A method as set forth in claims 8 and 20 wherein the optional fourth limit value is lower than the second limit value.

23. A method as set forth in claims 8 and 17 and 20, wherein the optional fifth limit value is lower than the second limit value and lower than the optional fourth limit value.

24. A method as set forth in claim 19, wherein the wood veneers bound for each separate category are organized relative to each other, such that the calculated dry densities thereof have moving averages which converge continuously towards an average predetermined for a particular category.

25. A method as set forth in claim 20 wherein the wood veneers bound for each separate category are organized relative to each other, such that the calculated dry densities thereof have moving averages which converge continuously towards an average predetermined for a particular category.

26. A method as set forth in claim 1, wherein the optical reflectivity of a wood veneer is measured for said analyzing over an entire wood veneer length and width; and this measurement of reflectivity is performed by illuminating one of the two wood veneer surfaces and by using an array of photosensitive detectors for measuring the amount of light reflected from this same wood veneer surface.

27. A method as set forth in claim 1, wherein the measurement for the optical reflectivity of a wood veneer for said analyzing is performed by means of electromagnetic radiation, having its wavelength within ultraviolet range or a visible range or an infrared range.

28. A method as set forth in claim 27, wherein the measurement for the optical reflectivity of a wood veneer is performed with a line camera, having a line of detectors set in a position transverse to a wood veneer progressing direction, or with an area camera.

29. A method as set forth in claim 1, wherein the measurement for the dry substance density of a wood veneer is performed with a radio-frequency electromagnetic resonator assembly, having its individual resonators set in a position transverse to a wood veneer progressing direction.

30. A method as set forth in claim 14, wherein a situation, in which the sorting process is supplied with wood veneers, whose calculated dry substance density is not capable of maintaining the moving average of dry substance densities with a sufficient accuracy at the predetermined average of dry substance density, results in:

setting off an alarm; and reserving a possibility of reducing the predetermined average of dry substance relative density for a limited period.

31. A method as set forth in claim 1, wherein said relatively lower and higher calculated dry substance density values either are actually lower and respectively higher than or equal with the initially measured values, or have lower and respectively higher or equal virtual values, which are modified from the initially measured values.

32. A method for increasing strength and/or reducing strength variations in multi-layer wood, plywood, or sandwich materials having a plurality of wood veneers one on the other, said method comprising the steps of:

measuring dry substance density, as well as longitudinal and lateral distributions of individual wood veneers, with a high-frequency electromagnetic resonance;

analyzing homogeneity and/or grain structure pf the individual wood veneers from a wood veneer surface on the basis of optical reflectivity of said surface represented by its darkness;

when said optical reflectivity indicates in the individual wood veneer:

I} a second type of darkness distribution deviating from a predominant darkness of the veneer surface, establishing a second calculated dry substance density value of the wood veneer in question for the sorting process; or II}a first type of darkness distribution in comparison with the predominant darkness of the veneer/veneers surface, establishing a first calculated dry substance density of the wood veneer in question for a sorting process;

sorting the wood veneers on the basis of said calculated dry substance densities for at least two different density categories, the dry substance density in a first density category being higher than in a second density category; and laying wood veneers on top of each other for building said multi-layer wood, plywood, or sandwich material, such that veneers graded in the first density category are placed as surface veneers, and veneers graded in the second density category are placed as central veneers.

33. A method as set forth in claim 32, wherein said second type of darkness distribution is a plurality of local first regions, which are substantially darker than the mean darkness of the veneer surface, and said second calculated dry substance density value is in a second way relatively lower than its initially measured value, and is used for selecting said wood veneer for said second density category.

34. A method as set forth in claim 32, wherein said first type of darkness distribution is a substantially uniform darkness, and said method further comprises a step of evaluating longitudinal and lateral distributions of the dry substance density in said wood veneer, and if those are substantially uniform, and said first calculated dry substance density of the wood veneer in question is in a first way relatively higher than its initially measured value, and is used for selecting said wood veneer for said first density category.

35. A method as set forth in any of claims 32, wherein the wood veneers bound for each separate category are organized relative to each other, such that the calculated dry densities thereof have moving averages which converge continuously towards an average predetermined for a particular category.

* * * * *